United States Patent [19]

Laurs et al.

[11] Patent Number: 4,992,384
[45] Date of Patent: Feb. 12, 1991

[54] MEASURING APPARATUS AND METHOD OF USE FOR ANALYZING A GAS MIXTURE

[75] Inventors: Heinz Laurs, Viersen; Hans-Peter Oepen, Niederzier, both of Fed. Rep. of Germany

[73] Assignee: Drägerwerk Aktiengesellschaft, Lübeck, Fed. Rep. of Germany

[21] Appl. No.: 239,442

[22] Filed: Sep. 1, 1988

[30] Foreign Application Priority Data

Sep. 2, 1987 [DE] Fed. Rep. of Germany ....... 3729286

[51] Int. Cl.$^5$ ...................... G01N 27/12; G01N 27/16
[52] U.S. Cl. ..................................... 436/151; 436/159; 422/88; 422/90; 422/98; 73/25.03
[58] Field of Search .............................. 422/88, 94–98, 422/107, 116, 93, 90–92; 436/126, 124, 151, 152, 159; 73/23, 27 R

[56] References Cited

U.S. PATENT DOCUMENTS

| | | | |
|---|---|---|---|
| 4,455,378 | 6/1984 | Heiland et al. | 422/98 |
| 4,670,405 | 6/1987 | Stetter et al. | 73/23 |
| 4,703,646 | 11/1987 | Müller et al. | 73/23 |

*Primary Examiner*—Christine Nucker
*Assistant Examiner*—William H. Beisner
*Attorney, Agent, or Firm*—Walter Ottesen

[57] ABSTRACT

The invention relates to a measuring apparatus for analyzing a gas mixture for at least one gas contained therein in a very low concentration. Such a gas can, for example, be anesthesia gas in ambient room air. The invention is directed to a type of apparatus wherein the gas mixture is split up into conversion products with a heated catalyzer element during measurement and wherein the conversion products are detected by means of a gas sensor which takes up at least one of the conversion products. The measuring apparatus makes possible a quasi-continuous monitoring of the ambient room air for an anesthesia gas with the aid of such sensors. In order to make this possible, a sequence of measuring phases and regeneration phases are cyclicly repeated. The measuring phases are very short in relationship to the response time of the sensor. During the regeneration phase, the catalyzer temperature is reduced so far and the sensor temperature is increased to the extent that the sensor releases more conversion products than it takes up. The regeneration phase in a cycle can be so controlled that the measuring quantity again has its initial value at the beginning of each new cycle.

16 Claims, 2 Drawing Sheets

MEASURING APPARATUS AND METHOD OF USE FOR ANALYZING A GAS MIXTURE

FIELD OF THE INVENTION

The invention relates to a measuring apparatus for analyzing a gas mixture for at least one gas contained therein at a very low concentration such as anesthesia gas made up of halogenated organic compounds. In this apparatus, the gas mixture is brought into contact with a heated catalyzer element during the measurement whereat the gas to be measured is split up into conversion products. The conversion products are detected by means of a gas sensor which takes up at least one of the conversion products while measurements are made with one measuring quantity of the sensor changing. In this apparatus, the gas sensor is brought into a regenerating state after the measurement by heating the same to a temperature increased with respect to the measuring state. In the regenerating state, the conversion products which were taken up are again released.

BACKGROUND OF THE INVENTION

Sensors are often utilized to detect gases operating pursuant to a measuring principle wherein the gas components which are sought are taken up by the sensor and cause a measuring quantity of the sensor to change.

An important example of such sensors are semiconductor sensors. These sensors are most often comprised of a thin layer made of semiconductive material which is disposed on an appropriate carrier. In this instance, the measuring quantity is the electrical resistance which changes because of the gas taken up.

Such sensors are, however, usually not sufficiently sensitive to detect very low concentrations of halogenated hydrocarbons. This applies especially to the detection of anesthesia gases in the air of a room. The permissible limit values lie in the range of a few ppm. A significant improvement was achieved in this area by means of the measuring apparatus described in U.S. Pat. No. 4,455,378. In this apparatus, an electrically heated catalyzer element is disposed in the vicinity of a sensor layer comprising phthalocyanine. The catalyzer element is preferably made of a metal taken from the series of the platinum metals. The anesthesia gas is converted to conversion products on the catalyzer element. The sensor reacts sensitively to the conversion products.

Such a measuring apparatus is suitable for the long-term observation of the air in a room with respect to anesthesia gas contained therein. If the sensor is exposed for several hours to the air in the room, then good measurable differences in the electrical resistance are obtained. However, a continuous observation of the corresponding gas concentrations is not possible in this manner. Furthermore, the long time duration during which the observation is made leads to falsifications of the measuring result especially because of the co-adsorption of foreign gases which, in the course of time, diminish the sensitivity of the sensor.

SUMMARY OF THE INVENTION

In view of the foregoing, it is an object of the invention to further develop gas measuring apparatus of the kind referred to above and especially insofar as they use sensors which have a slow response such that a quasi-continuous monitoring of the gas mixture is possible. Furthermore, the simplest handling possible is also desired.

The above object is achieved according to a feature of the invention in that the sequence of the measuring phases and the regeneration phases are cyclicly repeated with each cycle containing at least one measuring phase and one regeneration phase. A measuring phase is very much shorter than the time in which the sensor reaches 90% of its end value and, during a regeneration phase, the temperature of the catalyzer element is reduced so far and the temperature of the sensor is increased so much that the sensor releases more conversion products than it takes up.

Every sensor of the configuration utilized here has the characteristic that the measuring quantity approaches its end value asymptotically during the course of the time. This end value corresponds to the condition wherein the gas components in question have been taken up. Since the time until the end value is reached is not defined because of the asymptotic approach the time often selected for such sensors as a measure of the response characteristic is that time which passes until the sensor reaches 90% of its end value.

In the invention, an unusually short part of this time is utilized. Preferably, this time is less than 10% and less than 1% is especially preferred. Expressed in absolute values, the measuring phase preferably takes less than 60 seconds and less than 10 seconds is especially preferred.

During the regeneration phase, fewer conversion products occur because the catalyzer temperature is reduced. The increase of the temperature of the gas sensor leads to a change of the adsorption-desorption equilibrium in the sense that the adsorption reduces and the desorption increases. By means of these two measures, the condition is obtained that the sensor releases more conversion products during the regeneration phase than it takes up. In this way, the initial condition of a sensor is again achieved.

In the most simple case, the measuring phases and regeneration phases alternate with one another and a cycle consists of only a measuring phase and a regeneration phase. The regeneration phase is controlled such that at the beginning of the next measuring phase, the starting value of the measuring quantity (conductivity) is again obtained. However, for specific application purposes it is preferable to sequentially combine several measuring phases and regeneration phases in one cycle while then preferably so regulating at least one regeneration phase that the measuring quantity again reaches its initial value at the beginning of the new cycle.

The control of the regeneration phase can occur through the selection of the temperatures of the catalyzer element and/or the sensor or also by means of the duration of the regeneration. Generally, the regeneration takes place much faster the lower the temperature of the catalyzer element is and the higher the temperature of the sensor in the regeneration phase is. Measurements are conducted most simply by setting both values constant in the regeneration phase and controlling the regeneration over the time duration.

With the invention, the switchover from the measurement phase to the regeneration phase is achieved without movable elements simply in that the heating power of the catalyzer element and of the sensor are appropriately reswitched. Also, it is not necessary to conduct a reference gas across the sensor during the regeneration phase. Especially simple relationships are achieved when no detectable conversion product at all originates from the catalyzer element in the regeneration phase. This is realized in the simplest manner by switching off the heating current of the catalyzer element. Whether a conversion product detectable by the sensor occurs is, however, not only dependent upon the temperature of the catalyzer element; instead, it is also dependent on the sensitivity of the sensor and thereby on the temperature of the latter. The sensitivity is generally that much higher the lower the temperature is.

The apparatus according to the invention does not only operate faster than the known apparatus equipped with similar slow-acting sensors; but, the disturbing effects of the co-adsorption are significantly reduced by the cyclicly repeated regeneration and, in this way, a uniform sensitivity is obtained. Furthermore, an improvement of the specificity of the sensor is obtained, that is, there is a reduction of the influence of the gaseous components which do not correspond to the gas to be detected.

The specificity can be further increased by varying the temperature of the sensor and/or the temperature of the catalyzer element in the measuring phase and by evaluating the changes of the measuring quantity at the various temperatures.

The occurrence of various conversion products at the catalyzer element and their takeup in the sensor is as a rule in many ways dependent upon the temperature. For this reason, additional information is obtained from the measurements at different temperatures and this information can be utilized pursuant to known methods to analytically differentiate the concentrations of different conversion products from one another, thus yielding an increased specificity. This can be achieved by varying the temperatures within a measuring phase or also in different measuring phases of a cycle can be varied.

Another possibility for increasing the specificity is that several different gas sensors are utilized whic differ with reference to the dependence of the measuring quantity on the concentration of the conversion products. In a like manner to the above-mentioned case, the various changes of the measuring quantity can be utilized on the different sensors to analytically distinguish the concentration of the various conversion products.

BRIEF DESCRIPTION OF THE DRAWINGS

The invention will now be described with reference to the drawings wherein.

DESCRIPTION OF THE PREFERRED EMBODIMENTS OF THE INVENTION

The detection device 1 includes a flat cell 2 and a catalyzer element 3.

Figure 1:
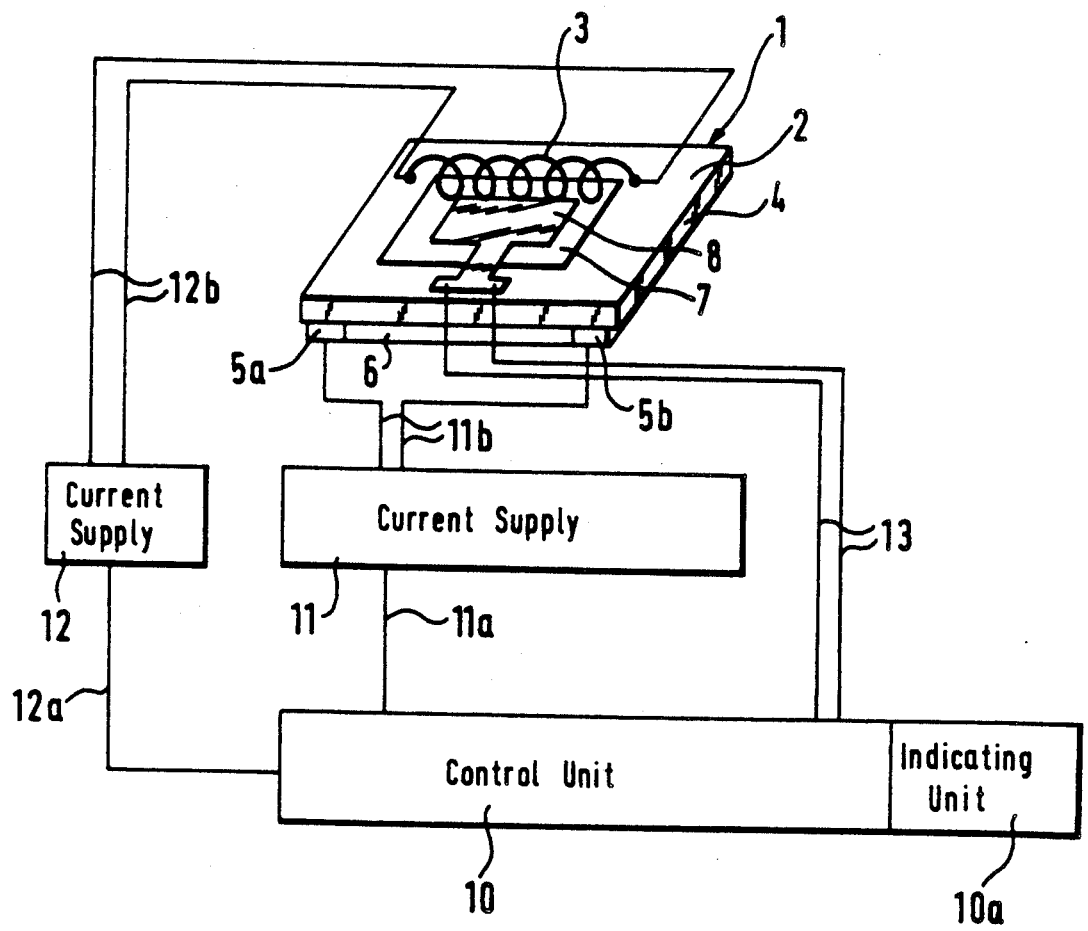
FIG. 1 shows the detection element configured as a flat cell interconnected with a measurement and evaluation circuit shown as a block diagram; and, FIG. 2 shows the time dependent course of the temperature of the catalyzer element and of the sensor layer as well as the conductance in a measuring and regeneration cycle.

The flat cell 2 has a ceramic carrier 4 having a heating element 6 disposed at its back side with the heating element 6 being provided with constant elements 5a and 5b. The actual gas sensor is located on the upper side of the ceramic carrier 4 as a thin layer 7 made of semiconductor material especially a material based upon phthalocyanine. Contact is made to respective sides of the sensor layer 7 by corresponding ones of vapor-deposited connecting electrodes 8 made of gold. The electrically separate electrodes 8 can not be seen separately in FIG. 1 because they are disposed one behind the other.

The catalyzer element is configured as a heatable platinum wire coil which is mounted in the free ambient room air approximately 10 mm ahead of the sensor layer 7 and is held in its position by a holder which is not illustrated for clarity.

The detection device 1 per se corresponds to known configurations. Details and the configuration of the detection element 1 are shown in U.S. Pat. No. 4,455,378 incorporated herein by reference.

The measuring and evaluation circuit has a central unit 10 which can be driven, for example, by a microprocessor. The central unit 10 controls the course of the measuring and regeneration phases and evaluates the received measuring signal.

The central control unit 10 controls respective current supplies 11 and 12 for the heat layer 6 of the sensor and for the catalyzer element 3. The control leads are identified in FIG. 1 by reference numerals 11a and 12a and the heating leads are identified by reference numerals 11b and 12.

The measuring signal from the gas sensor is taken off via measuring leads 13. The electrical resistance can be determined pursuant to known principles, for example, by measuring the current intensity at a known and constant predetermined voltage.

The central unit 10 is connected with an indicating unit 10a on which the measured results are displayed. It is understood that corresponding peripheral apparatus such as printers or display screens can be connected.

Figure 2:
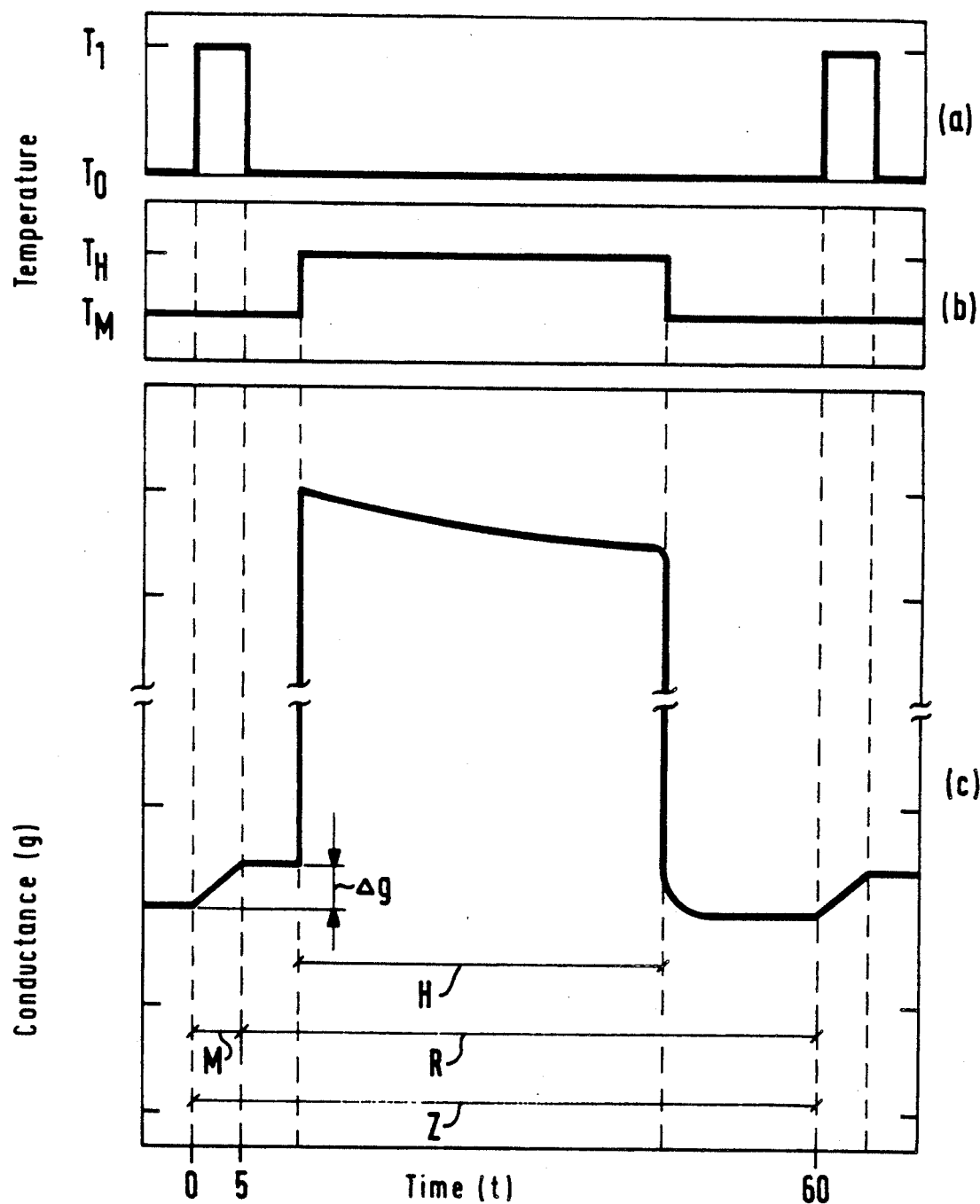

FIG. 2 shows a cycle comprising a measuring phase and a regeneration phase. Time (t) is measured along the abscissa. In the illustrated example, the measuring phase M begins at the time point $t=0$ and ends at $t=5$ seconds after which the regeneration phase R begins and has a duration which extends in the illustrated embodiment to $t=60$ seconds.

FIG. 2 comprises three component diagrams of which the uppermost component diagram (a) shows the temperature cycle of the catalyzer. At the beginning of the measuring phase, the catalyzer is heated from ambient room temperature to a constant increased temperature such as $T_1=700°$ C. at which the gas to be detected is catalytically split up into conversion products. The heating current of the catalyzer is switched off at the end of the measuring phase.

The second component diagram (b) shows the course of the temperature of the sensor layer 7. The sensor layer 7 is at a constant relatively low temperature (for example, $T_M=60°$ C.) at which the layer 7 has a good sensitivity for the conversion products (measuring state). Within the regeneration phase, the layer 7 is brought to an increased temperature such as $T_H=120°$ C. during a heating phase H at which the desorption exceeds the adsorption so that conversion products are released (regeneration state). The heating phase H lies completely in the regeneration phase R and can, however, be shorter than shown.

The lowest component diagram (c) of FIG. 2 shows the course of the measuring quantity of the sensor 7 which can, for example, be the conductance (g). The measuring quantity continues to increase during the measuring phase as shown. The rate of change is characteristic for the conversion products taken up by the sensor element 7 and so for the concentration of the gas to be determined. The rate of change can, for example, be specified as a differential quotient Δg/Δt. However, it can be preferable to determine the rate of change pursuant to other known principles of differential measurement.

When the catalyzer temperature is reduced at the beginning of the regeneration phase, conversion products are no longer taken up by the sensor element so that the measuring quantity (g) remains constant. The increase of the temperature of the sensor layer 7 immediately leads to an intense increase in the conductance (g). The conductivity falls off slowly because of the desorption of the conversion products and drops again to the initial value at the end of the heating phase H.

The regeneration phase R must be correspondingly controlled in order to obtain the condition that the conductive value again reaches the initial value at the beginning of a new cycle (t=60). As mentioned, this preferably occurs by controlling the duration of the regeneration of the gas sensor 7, that is, by correspondingly controlling the heating phase H. This is obtained, for example, by storing the total change of the measuring quantity Δg in the measuring phase and controlling the duration of the heating phase H in dependence upon Δg.

In the example of FIG. 2, a cycle comprises only one measuring phase and one regeneration phase. However, this is not always necessary. For example, several measuring phases with alternating regeneration phases having a constant runoff can be provided and only the last regeneration of a phase is so regulated that the measuring quantity again reaches its initial value at the beginning of the next measuring phase which belongs to the next cycle.

It is understood that the foregoing description is that of the preferred embodiments of the invention and that various changes and modifications may be made thereto without departing from the spirit and scope of the invention as defined in the appended claims.

What is claimed is:

1. A measuring apparatus for analyzing a gas mixture for at least one gas contained in the mixture at a very low concentration over a predetermined measurement duration, the measuring apparatus comprising:
   a heatable catalyzer exposable to said gas mixture during the measurement for splitting up said gas mixture into conversion products when said catalyzer is heated;
   a heatable gas sensor having a measuring quantity which can reach an end value at which the sensor is saturated and being operable in a measuring state at a first temperature during which at least one of said conversion products is taken up by the sensor causing a change in said measuring quantity and then being operable in a regeneration state at a second temperature higher than said first temperature during which said one conversion product is again released;
   control means connected to said sensor to control the temperature thereof so as to cause the same to go through a plurality of measuring cycles including a sequence of measuring and regeneration phases during which said sensor operates in said measuring and regeneration states, respectively, and each measuring cycle having one measuring phase and one regeneration phase with the measuring phase being very much shorter than said predetermined measurement duration and the time required for said measuring quantity to reach said end value at which the sensor is saturated; and,
   said control means also being connected to said catalyzer to reduce the temperature of the latter and to increase the temperature of said sensor during said regeneration phase of said measuring cycle so that said sensor releases more of said one conversion product than it takes up.

2. The measuring apparatus of claim 1, wherein the duration of said measuring phase is at most 10% of the time in which said measuring quantity of said sensor reaches 90% of said end value.

3. The measuring apparatus of cliam 1, wherein the duration of said measuring phase is at most 1% of the time in which said measuring quantity of said sensor reaches 90% of said end value.

4. The measuring apparatus of claim 1, wherein the duration of said measuring phase is less than 60 seconds.

5. The measuring apparatus of claim 1, wehrein the duration of said measuring phase is less than 10 seconds.

6. The measuring apparatus of claim 1, wherein the respective temperatures of said catalyzer and said sensor are constant in the measuring phase.

7. The measuring apparatus of claim 1, wherein the respective temperatures of the catalyzer and sensor are adjusted relative to each other during the regeneration phase so that the temperature of said catalyzer is reduced to a value whereat said gas mixture is no longer split up and the temperature of said sensor is increased to a value whereat said one conversion product is again released whereby no conversion product occurs which is detectable by said sensor.

8. The measuring apparatus of claim 1, wherein said stable catalyzer includes a metal selected from the platinum group and is heated to a temperature between 250° C. and 900° C. in the measuring phase; and, said sensor includes phthalocyanine and is heated in the measuring phase to a temperature between 30° C. and 100° C. and to a temperature between 100° C. and 200° C. in the regeneration phase.

9. The measuring apparatus of claim 1, wherein the sensor is brought up to a different temperature in each measuring phase of each of said measuring cycles and the change of the measuring quantity in each cycle is evaluated to analytically distinguish the concentrations of the different conversion products from each other.

10. The measuring apparatus of claim 1, wherein said heatable catalyzer is brought to a different temperature in each measuring phase of each of said measuring cycles and the change of the measuring quantity in each cycle at the different temperatures of the catalyzer element is evaluated to analytically distinguish the concentration of the different conversion products from each other.

11. The measuring apparatus of claim 1, comprising a plurality of said gas sensors which are distinguished from each other with reference to the dependency of the corresponding measuring quantity on the concentration of the conversion products; and, wherein the different changes of the measuring quantity of the different sensors are evaluated to analytically distinguish the concentrations of the different conversion products from each other.

12. A measuring appratus for analyzing a gas mixture for at least one gas contained in the mixture at a very low concentration over a predetermined measurment duration, the measuring apparatus comprising:

a heatable catalyzer exposable to said gas mixture during the measurement for splitting up said gas mixture into conversion products when said catalyzer is heated;

a heatable gas sensor having a measuring quantity which can reach an end value at which the sensor is saturated and being operable in a measuring state at a first temperature during which at least one of said conversion products is taken up by the sensor causing a change in said measuring quantity and then being operable in a regeneration state at a second temperature higher than said first temperature during which said one conversion product is again released;

control means connected to said sensor to control the temperature thereof so as to cause the same to go through a plurality of measuring cycles during said measurement duration beginning with a first measuring cycle and with each cycle including a sequence of measuring and regeneration phases during which said sensor operates in said measuring and regeneration states, respectively;

said measuring quantity having an initial value at the beginning of the first measuring cycle and each measuring cycle having one measuring phase and one regeneration phase;

said control means being adapted to cause said measuring phase to be very much shorter than the time required for said measuring quantity to reach said end value at which the sensor is saturated and to control the regeneration of said sensor during said regeneration of said sensor during said regeneration phase of each cycle so as to cause said measuring quantity to again reach said initial value at the end of each of said measurement cycles while at the same time causing said sensor to release more of said one conversion product than it takes up; and, said control means also being connected to said catalyzer to increase the temperature of said catalyzer at the beginning of the measuring phase and to reduce the temperature thereof at the end of the measuring phase.

13. The measuring apparatus of claim 12, with said control means being adapted so as to cause said measuring quantity to be at said initial value at the beginning of each measuring cycle.

14. The measuring apparatus of claim 12, wherein each of said measuring cycles has a plurality of measuring phases and a plurality of regeneration phases alternating with said measuring phases with each measuring cycle ending with a last regeneration phase; and, said control means being adapted to control the regeneration of said sensor during said last regeneration phase of each cycle so as to cause said measuring quantity to again reach said initial value at the end of each of said measuring cycles.

15. A method of analyzing a gas mixture for at least one gas contained in the mixture at a very low concentration over a predetermined measurement duration including a plurality of measurement cycles with each other having at least one measuring phase and at least one regeneration phase, the method being conducted with the aid of a heatable catalyzer and a heatable gas sensor with the gas sensor having a measuring quantity which has an initial value at the beginning of the first measuring cycle and which can reach an end value at which the sensor is saturated, the method comprising the steps of:

heating the catalyzer exposed to said gas mixture to a first temperature during each measuring phase of each measurement cycle for splitting up said gas mixture into conversion products and controlling the catalyzer to a second temperature less than said first temperature during the regeneration phase;

heating the sensor to a first temperature during said measuring phase during which at least one of said conversion products is taken up by the sensor causing a change in said measuring quantity and then heating the sensor to a second temperature higher than said first temperature during said regeneration phase thereby causing said one conversion product to be released, said sensor being heated so as to cause said measuring phase to be very much shorter than said measurement duration and the time required for said measuring quantity to reach said end value; and, controlling the heating of the catalyzer and the sensor to cause the apparatus to go through a plurality of said measuring cycles and controlling the heating of said sensor during said regeneration phase so as to cause said measuring value to again reach said initial value at the end of said measurement duration.

16. The method of claim 15, wherein each measuring cycle has a plurality of measuring phases and a plurality of regeneration phases alternating with said measuring phases with each measuring cycle ending with a last regeneration phase; and, the heating of said sensor is controlled during said last regeneration phase so as to cause said measuring value to again reach said initial value at the end of said measurement duration.

* * * * *

UNITED STATES PATENT AND TRADEMARK OFFICE
CERTIFICATE OF CORRECTION

PATENT NO. : 4,992,384

DATED : February 12, 1991

INVENTOR(S) : Heinz Laurs and Hans-Peter Oepen

It is certified that error appears in the above-identified patent and that said Letters Patent is hereby corrected as shown below:

In column 2, line 20: delete "approach" and substitute -- approach, -- therefor.

In column 3, line 39: delete "whic" and substitute -- which -- therefor.

In column 3, line 64: delete "constant" and substitute -- contact -- therefor.

In column 4, line 24: delete "12." and substitute -- 12b. -- therefor.

In column 6, line 13: delete "cliam 1," and substitute -- claim 1, -- therefor.

In column 6, line 19: delete "wehrein" and substitute -- wherein -- therefor.

In column 6, line 35: delete "stable" and substitute -- heatable -- therefor.

UNITED STATES PATENT AND TRADEMARK OFFICE
CERTIFICATE OF CORRECTION

PATENT NO. : 4,992,384

DATED : February 12, 1991

INVENTOR(S) : Heinz Laurs and Hans-Peter Oepen

It is certified that error appears in the above-identified patent and that said Letters Patent is hereby corrected as shown below:

In column 6, line 43: delete "up".

In column 6, line 67: delete "measurment" and substitute -- measurement -- therefor.

In column 7, delete line 32 and substitute -- regenera- -- therefor.

In column 8, line 10: delete "other" and substitute -- cycle -- therefor.

Signed and Sealed this

Twenty-eighth Day of July, 1992

Attest:

DOUGLAS B. COMER

Attesting Officer     Acting Commissioner of Patents and Trademarks